United States Patent [19]

Balducci et al.

[11] 4,105,588

[45] Aug. 8, 1978

[54] PREPARATION OF COPPER AND SILVER PARTICLES FOR ETHYLENE PURIFICATION

[75] Inventors: Agostino Balducci, San Donato Milanese; Margherita Corbellini, Milan; Vittorio Mormino, San Donato Milanese; Bruno Notari, San Donato Milanese; Luigi Rivola, San Donato Milanese, all of Italy

[73] Assignee: Snam Progetti, S.p.A., San Donato Milanese, Italy

[21] Appl. No.: 804,382

[22] Filed: Jun. 7, 1977

Related U.S. Application Data

[60] Continuation of Ser. No. 574,910, May 6, 1975, abandoned, which is a division of Ser. No. 422,743, Dec. 7, 1973, abandoned.

[30] Foreign Application Priority Data

Dec. 20, 1972 [IT] Italy ............................... 33278 A/72

[51] Int. Cl.$^2$ ..................... B01J 29/00; B01J 29/06; B01J 21/00
[52] U.S. Cl. ............................ 252/454; 252/455 Z; 252/463; 260/677 A
[58] Field of Search .................. 260/677 A; 252/454, 252/455 Z, 463

[56] References Cited

U.S. PATENT DOCUMENTS

3,676,516 7/1972 Haskell et al. .................. 260/677 A
3,720,604 3/1973 Rosback ......................... 260/677 A

FOREIGN PATENT DOCUMENTS

687,613 3/1966 Belgium.

*Primary Examiner*—Veronica O'Keefe
*Attorney, Agent, or Firm*—Morgan, Finnegan, Pine, Foley & Lee

[57] ABSTRACT

Process for the purification of olefins by removing oxygen and acetylene from them which comprises passing the olefins over a contact material consisting essentially of a metallic element from the first B group of the period system which element is homogeneously and finely dispersed on a carrier selected from zeolites, spheroidal alumina, silica gel, Kieselghur or colloidal silica stabilized in an aqueous suspension. The purification process is carried out at temperatures of from −50 to 50° C under pressures of from 0.01 to 60 atmospheres. The contact material is prepared by mixing a suitable compound of the metallic element such as a carbonate or ammonia complex with the selected carrier, thereafter atomizing the mixture to obtain microspheroids, granulating the spheroids into the desired shape and size and finally subjecting the carrier material to a reducing treatment to obtain the metallic element thereon. The contact material for the purification preferably utilizes the element copper with the contact material having the size of 1–250μ and is most suitably used in the purification of ethylene.

3 Claims, No Drawings

PREPARATION OF COPPER AND SILVER PARTICLES FOR ETHYLENE PURIFICATION

This is a continuation, of application Ser. No. 574,910 filed May 6, 1975, which, in turn, was a division of prior application, Ser. No. 422,743, filed Dec. 7, 1973 and now both abandoned.

The present invention relates to a material suitable for the purification of olefins, to a process for use in preparing such material and to a process for the purification of olefins employing said material.

It is known that olefins can be purified by removing oxygen through processes based on the employment of absorbents such as silica, aluminium or iron oxides, activated carbon, silica gel, molecular sieves, or cupric oxide. However, those methods suffer from serious drawbacks because of the requirements and conditions of such treatments. For instance they are generally carried out at high temperatures which give rise to secondary reactions such as, in the case of the ethylene purification for example, the formation of low molecular weight dimers or oligomers, which in turn remarkably decrease the activity of the catalyst.

The Belgian Pat. No. 687,613, of Farbwerke Hoechst, points out such drawbacks the absorbent materials mentioned and discloses a process for the purification of olefins based on the employment of finely subdivided copper deposited on diatomaceous earth.

The catalyst removes the impurities, particularly in the case of ethylene by simultaneously retaining acetylene and oxygen, which react with the copper to form an acetylide and oxides respectively, together with water which is retained by the microporous carrier, while operating at a moderate temperature.

The material referred to in the Hoechst patent is obtained by reacting copper sulphate and sodium carbonate in presence of diatomaceous earth to produce copper basic carbonate, adding magnesium basic carbonate to the obtained mass and then reducing under a hydrogen stream and at such a temperature as to remove the water of reaction. The employment, in the purification of olefins, of a material prepared according to the Hoechst patent, may produce good results, but they are not consistently reproducible since the method used for preparation of the absorbing material does not always produce homogeneously dispersed powders.

Intimate mixing of the metal and the carrier is not assured, and this decreases the active surface available, which in turn substantially decreases the specific activity of the subsequent purification treatments.

In addition, the use of a different substance, i.e., magnesium basic carbonate, increases the difficulties of reproducing the absorbent properties of the material.

We have now found, which is a first aspect of our invention, that it is possible to obtain a high efficiency and a very high reproducibility in the purification of olefins by using contact materials consisting of metals belonging to the 1st B group of the element periodic system (Handbook of chemistry and physics, the 39th edition, by Chem. Rubber Publ. Co. - Cleveland) which are finely and homogeneously dispersed on carriers selected from zeolites, spheroidal alumina, silica gel, Kieselguhr or colloidal silica stabilized in an aqueous suspension. The contact materials of our invention are obtained by a process, constituting a further aspect of the invention, which gives rise to powders of highly and homogeneously dispersed materials, which also have a controlled granularity.

This method, in contrast to the ones previously known, produces a contact material having the desired sizes and an active surface which is the most efficacious for the subsequent uses. The reproducibility of good results is therefore insured by controlling the mixing of the metal and the carrier. This removes the possibility that at the end of the preparation any roughly dispersed metal particles will be present. As a result of this, during the olefins purification, it is now possible to use minimum amounts of the metal itself and, hence, a higher economy in the whole purification process is achieved.

The preparation method of the contact material according to the present invention fundamentally consists in preparing a suitable compound of a metallic element of the first B group of the Periodic System, suspendable or soluble, for example the basic carbonate or the ammonia complex in the case of copper, and adding the chosen carrier to the metal compound, then atomizing the mixture to obtain microspheroid powder of the material, then granulating this powder to give it the most suitable shape and sizes in view of the absorbing process (tabletting, etc.), then subjecting the material to a reducing process to obtain the metallic element.

The atomization may be carried out starting from solutions or suspensions containing all of the components. Powders of highly and homogeneously dispersed materials, having a controllable granularity, are produced by controlling parameters such as the concentration of the starting solutions and the speed of the turbine nebulizing the liquid. The operation is carried out at a temperature of from 110° to 500° C and produces particles having sizes of from 1 to 250 $\mu$.

The purification of olefins using the contact material of this invention is carried out at slightly low temperatures ranging from −50 to +50° C and at pressures of from 0.01 to 60 atmospheres. The olefin is passed through the contact mass until the activity thereof ceases. The contact mass may contain the metal in an amount of from 1 to 50% and preferably 5 to 25% by weight. After purification treatment of the olefin absorbent material is subjected to a regeneration process carried out according to well known techniques, usually employed in the copper acetylides treatment.

Further details of our invention will become clear upon consideration of the following illustrative, non-restrictive, examples.

EXAMPLE 1

(a) This example relates to the preparation of 300 Kg of $Cu/SiO_2$. 200 Kg of $CuSO_4 \cdot 5H_2O$ are dissolved into 2,000 liters of deionized water. Separately 84.9 Kg of $Na_2CO_3$ are dissolved into 1,300 liters of deionized water. The latter solution is then slowly added to the $CuSO_4$ solution with continuous, vigorous stirring. Copper basic carbonate precipitates, and is recovered by centrifuging and is washed with $H_2O$ containing $CO_2$ (in order to avoid the hydrolysis up to the formation of a more basic carbonate difficulty soluble in $NH_4OH$) until the sulphate ion is not detectable.

500 Kg of an aqueous ammonia 43% solution is dissolved into deionized water to a volume of 3,200 liters. All of the copper basic carbonate is solubilized into this solution. Following complete dissolution of the copper basic carbonate, 1,333 kg of $SiO_2$ Ludox AS 30 are added. The mixture is mixed with air at 300° C. It is then atomized, maintaining an output temperature of 150° C with the nebulizing turbine turning at 7,500 r.p.m. Following this process 300 Kg of material are obtained. A portion thereof is collected in the lower part of the atomizer and the remaining portion collected in the centrifugal separator of the powder from air.

Use is made of the powder collected by the centrifugal separator having average sizes equal to 50 μ.

The powder is extruded in the form of cylinders after adding 800 g of an aqueous solution of 1.5% of Methocel HG 400 per 1 Kg of powder. Little cylinders are obtained having 2 mm φ and 8 mm height.

The cylindrical material thus obtained is first dried in a stove at 120° C and then subjected, under a nitrogen stream, to a gradual increase of temperature. At 200° C little hydrogen impulse charges are sent through the nitrogen feed line.

The amounts of such charges are such that they reduce the powder material without causing extreme overheating. As soon as the temperature returns to where it started, the hydrogen injection is performed. This operation is repeated until further hydrogen injections do not cause any temperature increases. Then the nitrogen is completely replaced by hydrogen and the treatment continued for another 30 minutes in order to insure the complete reduction of the copper. Then nitrogen is fed again and the mass cooled down to room temperature. The reduced material must be stored under dry nitrogen.

The material thus obtained is utilized for the purification of ethylene to be employed in a high yield polymerization process.

The ethylene purification validity is determined only by the polymerization yields, which is the most reliable method since the ethylene impurities are present in such amounts that they are not analytically measurable. 1 liter of n-heptane containing 1 mmole of AlEt$_3$ was introduced into a Pfauder autoclave having 4 l capacity, from which water and air had been removed, in order to wash it. The mixture is stirred at 85° C for about 80 minutes and then the washing heptane is discharged. Again 2.5 liters of n-heptane are introduced containing 12 mg of AlEt$_3$ by means of an ethylene stream. Separately 0.09 n grat. of TiCl$_3$.AA are prepared in 300 ml of n-heptane and then charged into the autoclave. By means of a thermostat the temperature is maintained at 85° C and the ethylene pressure is brought to 6 kg/cm$^2$.

The polymerization is followed by a flowmeter.

After 5 hours the autoclave is opened and discharged, the polymer is centrifuged, dried and weighed.

The ethylene is passed through a scrubber contained in a stainless steel column.

The polymer yield (expressed by polymer kg per Ti gram after 5 hours) is 81% at a specific activity of 2.62. By specific activity we mean the polymer kg per titanium gram per kg/cm$^2$ of ethylene.

(b) The same test is repeated but by doubling the turbine velocity in atomizing the copper - silica composition (1,500 rounds per minute). Novel particle sizes were obtained equal to 10 μ.

The copper amount of the final absorbent product is 10%. The polymerization of ethylene, utilizing this purifying system, gives a 93% yield at a specific activity of the purifying system, equal to 3.18. Therefore the lower the sizes of the atomized material the higher the specific activity of the absorbing material.

(c) Comparative tests are carried out by conducting the polymerization under the same conditions without purifying the ethylene with the inventive purifying system or using a molecular sieves to purify it.

The following results are obtained:

| Test | Yield | Specific activity |
|---|---|---|
| without any purifying system | 58 | 1.87 |
| with molecular sieves | 68 | 2.18 |

EXAMPLE 2

This example shows the effectiveness of an Ag/zeolite Y composition as the absorbing agent.

240 g of AgNO$_3$ are dissolved into 1.5 liters of deionized water. In this solution, there are then suspended g 450 of sodium zeolite Y SK 40 of Union Carbide. The suspension is vigorously stirred for two hours and then decanted.

The solid is washed four times with deionized water and then dried in a stove at 120° C for one night. The dried material is calcined for three hours in a quartz pipe at 230° C under a nitrogen stream, then the temperature is raised to 420° C while a N$_2$-H$_2$ mixture is flowed over it. The zeolite containing the reduced Ag is again pulped in 2.5 liters of deionized water containing 70 g of NaNO$_3$, and stirred vigorously for two hours, decanted, washed, and finally dried in a stove at 260° C for one night. The final product is analyzed and the Ag content is 22%.

By using this material as absorber in the ethylene polymerization process according to Example 1, a polymer yield of 84% was obtained at a specific activity of 2.72.

EXAMPLE 3

This example shows the effectiveness of a Cu/zeolite Y composition as absorber.

The process for preparing this sample is similar to the one in Example 2. The cupric salt solution contained g 255 of Cu(NO$_3$)$_2$.3H$_2$O per solution liter. 1.5 liters of solution are employed in order to suspend g 400 of zeolite. Copper content = 18%.

Using this material as absorber in the ethylene polymerization process according to Example 1 a polymer yield of 91% is obtained at a specific activity of 2.94.

EXAMPLE 4

This example shows the effectiveness of a Cu/Al$_2$O$_3$ composition as absorber.

In order to prepare this sample use is made of an Al$_2$O$_3$ carrier in the form of spheres having 1.5 diameter, 0.8 cc/g total porosity, 350 m$^2$/g surface area.

400 g of spheroidal alumina are impregnated by 300 cc of a solution containing 30% of Cu nitrate. The solution is completely absorbed by the carrier. The material is calcined under an air stream at 350° C for 6 hours and then reduced in a pipe by a N$_2$ + H$_2$ mixture at 300° C for 2 hours. The Cu content of the final product is 18%.

By using this Cu material as absorber in the ethylene polymerization process of Example 1 a 76% polymer yield is obtained at a specific activity of 2.45.

EXAMPLE 5

This example shows the effectiveness of an Ag/Al$_2$O$_3$ composition as absorber. The same carrier of Example 4 is impregnated with an aqueous solution of Ag lactate containing 28% Ag. After the excess impregation and the removal of the solution, the material is dried at 120° C, for one night, in a stove under a chromatographic air stream and finally calcined at 340° C for 4 hours.

The final product contains 15% Ag.

By using this material as absorber in the ethylene polymerization process according to Example 1, a 71% polymer yield is obtained at a specific activity of 2.20.

What we claim is:

1. The process of preparing a contact material adapted for use in the purification of ethylene said contact material consisting of from 1 to 50% by weight of particles of a finely divided elemental metal selected from Cu and Ag homogeneously dispersed on a carrier selected from the group consisting of zeolites, spheroidal alumina, silica gel, Kieselguhr and colloidal silica, which comprises forming a solution or suspension of a reducible compound of said metal, mixing said carrier therewith, atomizing said mixture at a temperature of from 100° to 500° C so that particles having sizes of from 1 to 250 $\mu$ are produced, granulating said particles, and then reducing said compound of said metal to said elemental metal.

2. The process of preparing a contact material as claimed in claim 1, wherein said metal is copper.

3. The process of preparing a contact material as claimed in claim 1, wherein said metal is silver.

* * * * *